United States Patent [19]
Lee

[11] Patent Number: 6,074,648
[45] Date of Patent: Jun. 13, 2000

[54] GALENIC PREPARATION FOR PREVENTION AND TREATMENT OF HEPATOCARCINOMA

[75] Inventor: Jung Sik Lee, Seoul, Rep. of Korea

[73] Assignee: Sam Chun Dang Pharm Co., Ltd., Seoul, Rep. of Korea

[21] Appl. No.: 09/130,488

[22] Filed: Aug. 7, 1998

[30] Foreign Application Priority Data

Nov. 5, 1997 [KR] Rep. of Korea ............... 97-58133

[51] Int. Cl.⁷ .................................................. A61K 35/78
[52] U.S. Cl. ........................................................ 424/195.1
[58] Field of Search ......................................... 424/195.1

[56] References Cited

U.S. PATENT DOCUMENTS 5,482,711  1/1996  Medenica ........................ 424/195.1
5,837,257  11/1998  Tsai et al. ....................... 424/195.1

FOREIGN PATENT DOCUMENTS 113805  11/1994  Switzerland .
112460  9/1995  Switzerland .
WO 97/02831  1/1997  WIPO .

*Primary Examiner*—Ralph Gitomer
*Attorney, Agent, or Firm*—Birch, Stewart, Kolasch & Birch, LLP

[57] ABSTRACT

The present invention relates to a galenic preparation for prevention and treatment of hepatocarcinoma. More specifically, the present invention relates to a galenic preparation which comprises an injectable composition having a good preventive and therapeutic effect particularly against hepatitis B virus and containing 4 kinds of main natural drugs, i.e., *Hedyotidis herba, Curcumae longae rhizoma, Polygonati cuspidati radix* and *Sophorae tonkinesis radix*; and an oral composition having a preventive and therapeutic effect against fatty liver and hepatic cirrhosis and containing 10 kinds of natural drugs, i.e., *Hedyotidis herba, Paridis rhizoma, Polygoni cuspidati rhizoma, Sophorae tonkinesis radix, Gentianae scabrae radix, Rhei rhizoma, Forsythiae fructus, Paeoniae radix rubra, Curcumae longae rhizoma* and *Acori graminei rhizoma*, and which can effectively prevent the development of hepatic diseases including hepatitis, fatty liver and hepatic cirrhosis into hepatocarcinoma and treat hepatocarcinoma by combined administration of two kinds of the compositions.

5 Claims, 3 Drawing Sheets

GALENIC PREPARATION FOR PREVENTION AND TREATMENT OF HEPATOCARCINOMA

TECHNICAL FIELD

The present invention relates to a galenic preparation for prevention and treatment of hepatocarcinoma. More specifically, the present invention relates to a galenic preparation which comprises an injectable composition having a good preventive and therapeutic effect particularly against viral hepatitis B and containing 4 kinds of main natural drugs, i.e., *Hedyotidis herba, Curcumae longae rhizoma, Polygoni cuspidati radix* and *Sophorae tonlkinesis radix*; and an oral composition having a preventive and therapeutic effect against fatty liver and hepatic cirrhosis and containing 10 kinds of natural drugs, i.e., *Hedyotidis herba, Paridis rhizoma, Polygoni cuspidati radix, Sophorae tonkinesis radix, Gentianae scabrae radix, Rhei rhizoma, Forsythiae fructus, Paeoniae radix rubra, Curcumae longae rhizoma* and *Acori graminei rhizoma*, and which can effectively prevent the development of hepatic diseases including hepatitis, fatty liver and hepatic cirrhosis into hepatocarcinoma and treat hepatocarcinoma by combined administration of two kinds of the compositions.

BACKGROUND ART

The etiology of hepatocarcinoma have not yet been clearly established. However, hepatocarcinoma is statistically characterized by the fact that the incidence rate is higher in men, rather than in women, who are in their forties to sixties, and it may be accompanied by hepatic cirrhosis in approximately 80% and by hepatitis C in 10%. Such characteristics are consistent with the fact that the areas in which hepatocarcinoma is predominant, such as Far east and East South Asia including Korea, Southern Europe, Africa, etc. also has a high frequency of hepatitis B virus carrier. In these areas, it may be found that hepatocarcinoma attacks in the group of one family. Further, chronic hepatic disorders including hepatic cirrhosis, chronic hepatitis, etc. have a relatively high tendency to develop hepatocarcinoma, regardless of hepatitis B and C. In addition, it has been known that the frequency to develop hepatocarcinoma from chronic hepatitis and hepatic cirrhosis may be increased 6–8 times by alcohol intake or smoking.

In many cases, hepatocarcinoma shows its unique symptoms only after it is considerably aggravated. Hepatocarcinoma shows various symptoms which include, generalized ones, such as systemic malais, anorexia, etc., hypertrophy of liver at right epigastrium and formation of mass in liver, and further a general deteriorated symptoms of hepatic cirrhosis such as ascites, jaundice, spleen hypertrophy, etc.

Up to date, the excision of the cancerated poition of liver has been considered as the most effective method for treatment of hepatocarcinoma. However, the use of such excision surgery is limited depending on the condition of hepatocarcinoma. For instance, the excision surgery cannot be applied to a person who suffers from serious hepatic cirrhosis as a secondary condition, even though his hepatocarcinoma is small and is found by early diagnosis. In addition, when hepatocarcinoma is under 3 cm, the means wherein alcohol is directly injected into cancerated portion under ultrasonographic observation to completely destruct the cancer may be utilized. Although this method has a superior effect and shows the course similar to that after surgical excision, it has substantially no effect on cancerous tumors which are greater than 3 cm.

In the case where the surgical operation may bring about fatal risk to a person suffering from hepatocarcinoma because he also suffers from considerably aggravated hepatic cirrhosis, the use of anti-cancer agents is suggested. For such a case, the administration of anti-cancer agents through oral route or common injection does not provide substantial effect but the therapeutic method either wherein the anti-cancer agent is directly injected into the cancerated liver tissue through a hepatic artery or wherein the anti-cancer agent is administered and then the blood vessel connected to the cancerated portion is occluded is mainly utilized.

Since many hepatocarcinoma tumors may lead to death, the prophylaxis of hepatocarcinoma must be prior to the therapeutic treatment of hepatocarcinoma which is already invaded. In present, the only method for prophylaxis of hepatocarcinoma is inoculation of a vaccine preparation.

Under such a situation, the present inventors have extensively studied to develop the drug which can effectively treat hepatocarcinomna and also prevent the development of hepatocarcinoma by inhibiting the progress of hepatic cirrhosis to hepatocarcinoma, particularly, using numerous compositions produced by combining various natural drugs which have been disclosed as having relatively little toxicity and side effects. As a result, we have identified that the purpose as mentioned above can be effectively attained by the combined administration of an injectable composition and an oral composition, each of which has a unique constitution as defined below, and thus completed the present invention.

DISCLOSURE OF THE INVENTION

Thus, the present invention relates to a galenic preparation useful for prevention and treatment of hepatocarcinioma.

Particularly, the present invention relates to a galenic preparation in the form of a kit, which is effective for preventing the development of hepatocarcinoma by inhibiting the progress of hepatitis or hepatic cirrhosis to hepatocarcinoma and for theating hepatocarcinoma, by combined administration of an injectable composition having a good preventive and therapeutic effect against hepatitis B virus and an oral composition having a preventive and therapeutic effect against fatty liver and hepatic cirrhosis.

More specifically, the present invention relates to a galenic preparation useful for the prevention and treatment of hepatocarcinoma which comprises an injectable composition (A) having a therapeutic effect against hepatitis B virus and containing 4 kinds of main natural drugs, i.e. *Hedyotidis herba, Curcumae longae rhizoma, Polygoni cuspidati radix* and *Sophorae tonkinesis radix*, and an oral composition (B) having a preventive and therapeutic effect against fatty liver and hepatic cirrhosis and containing 10 kinds of natural drugs, i.e. *Hedyotidis herba, Paridis rhizoma, Polygoni cuspidati radix, Sophorae tonkinesis radix, Gentianae scabrae radix, Rhei rhizoma, Forsythiae fructus, Paeoniae radix rubira, Curcumae longae rhizoma* and *Acori graminei rhizoma*. The galenic preparation of the present invention can effectively treat hepatocarcinoma without using surgical operation or anti-cancer agents, and also effectively prevent the development of hepatic disorders such as hepatic cirrhosis into hepatocarcinoma.

BRIEF DESCRIPTION OF DRAWINGS

For a thorough understanding of the nature and objects of the invention, reference should be made to the following detailed description taken in connection with the accompanying drawings in which.

BEST MODE FOR CARRYING OUT THE INVENTION

Figure 1:
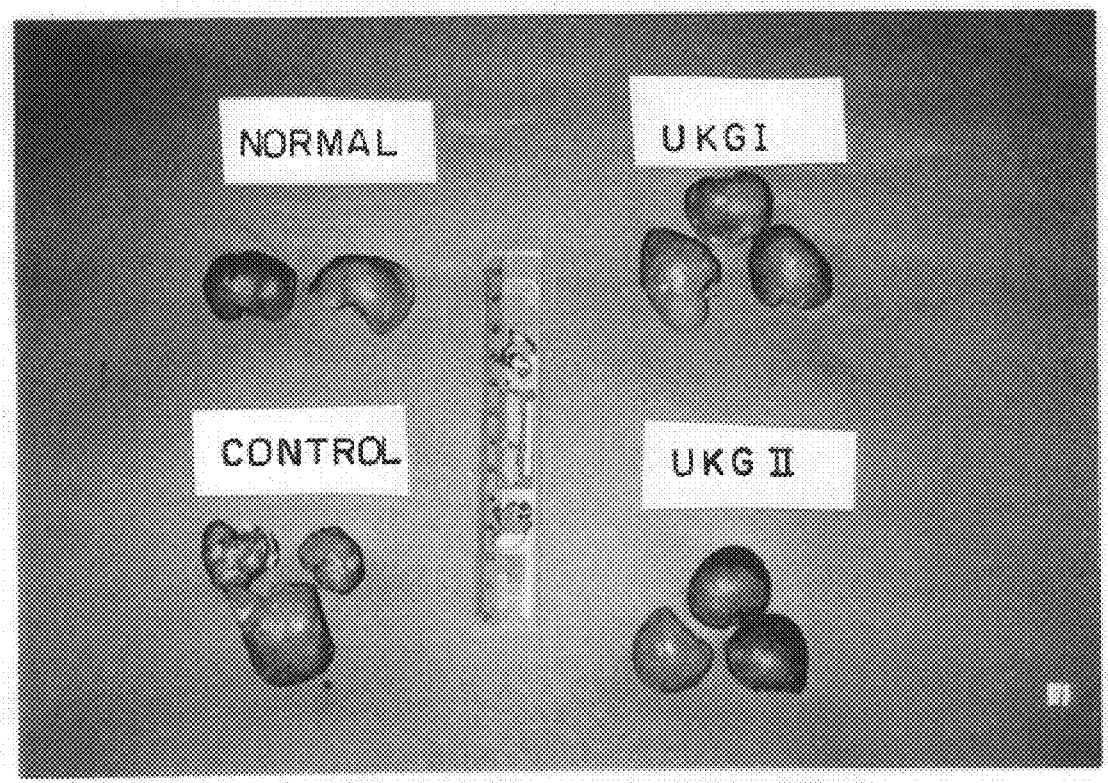
FIG. 1 is a photograph of rat liver having chronic hepatocarcinoma induced by DEN (diethylnitrosoamine) and AAF (acetaminofluorene) according to Experiment 6 (Normal, (normal group): a group to which only physiological saline is administered, Control (control group): a group to which DEN and AAF are only administered; UKG1 (test group 1): a group to which 40 mg/kg of the oral composition (B) is administered via oral route and 70 μl/kg of injectable composition (A) is intraperitoneally administered, UKG2 (test group 2): a group to which 200 mg/kg of the oral composition (B) is administered via oral route and 350 μl/kg of injectable composition (A) is intraperitoneally administered.

As one part constituting the galenic preparation of the present invention, the injectable composition (A) which is produced by combining 4 kinds of main natural drugs, i.e. *Hedyotidis herba, Curcumae longae rhizoma, Polygoni cuspidati radix* and *Sophorae tonkinesis radix*, has a preventive and therapeutic effect against viral hepatitis by enhancing the immunological function and exhibiting anti-viral activity, due to various pharmacological activities of the main natural drugs. As another part of the galenic preparation of the present invention, the oral composition (B) which is produced by combining 10 kinds of main natural drugs, i.e. *Hedyotidis herba, Paridis rhizoma, Polygoni cuspidati radix, Sophorae tonkinesis radix, Gentianae scabrae radix, Rhei rhizoma, Forsythiae fructus, Paeoniae radix rubra, Curcumae longae rhizoma* and *Acori graminei rhizoma* has a preventive and therapeutic effect against hepatic cirrhosis based on numerous pharmacological activities of main natural drugs. In the galenic preparation of the present invention, hepatocarcinoma which may be readily developed from chronic viral hepatitis B or hepatic cirrhosis can be effectively prevented and treated by administering these two compositions altogether.

Hereinafter, the complex effect of the composition of the present invention for prevention and treatment of hepatocarcinioma, which is originated from the pharmacological activities of respective main natural drugs is specifically explained.

It has been known that *Hedyotidis herba* acts mainly on the heart and liver an exhibits anti-cancer, anti-bacterial and anti-inflammatory activities and to inhibit HBsAg and reduce SGPT. It also has a blood cleaning and detoxicating effect so that it can be effectively used for jaundice and hepatic disorders such as viral hepatitis. It is a substantially non-toxic natural drug having the $LD_{50}$ value of 104 g/kg (mouse, i.p.) as the standard of toxicity.

*Curcumae longae rhizoma* increases the secretion of bile juice and the contraction of gall-bladder, and exhibits a cholagogic activity by normalizing the contents of bile juice. It has also been known that *Curcumae longae rhizoma* has a superior anti-bacterial activity and therefore, prolongs the survival period of mouse infected with hepatitis virus and that exhibits a superior therapeutic effect against viral hepatitis and hepatic disorders caused by chemical substances (carbon tetrachloride). In "Efficacy & Treatment", item 8 at page 476 (third column) of Grand Dictionary of Chinese Medicine, Vol. I, printed on Dec. 10, 1985 in Japan, it is disclosed that *Curcumae longae rhizoma* acts as a stomachic and aromatic to promote the detoxification of the bile duct and liver and therefore, can be used for the treatment of jaundice, cardiagra, etc.

*Polygoni cuspidati radix* has anti-bacterial and anti-viral activities and may be intravenously injected under shock conditions resulting firm hypoglycemia. Meanwhile, "Character and Combination & Contraindications" at page 837 (third column) of Grand Dictionary of Chinese Medicine, Vol. II, printed on Dec. 10, 1985 in Japan discloses that *Polygoni cuspidati radix* is non-toxic but is contraindicated in pregnant woman.

It is recognized that the anti-tumor activity of *Sophorae tonkinesis radix* is effective in vitro test against mouse ascitic cancer. In addition, "Gaeboboncho" discloses that *Sophorae tonkinesis radix* removes the toxicity of numerous drugs and the poison at the wound site, has an analgesic activity, an d also can tieat acute jaundice, tussis, fervescence, etc.

*Paridis rhizoma* has a detoxicating activity to treat hepatic damage caused by alcohol and enhances the immunological function in human body. It has also been noted that *Paridis rhizoma* can exhibit an anti-cancer activity when it is used in a large amount.

It has been known that *Rhei rhizoma* has anti-bacterial, anti-tumor and cathartic activities and can treat sarcomatous change of thyroid gland, degeneration of hepatic cells, congestion of hepatic vein, etc. Further, when *Rhei rhizoma* is administered to human body, it is mainly distributed in liver and kidney to show its activities. Recently, it has also been found that *Rhei rhizoma* has phannacological activities similar to those of interferons.

*Forsythiae fructus* has a potent anti-bacterial activity, acts mainly on heart, liver and gall-bladder, and is non-toxic. In addition, it has been discovered that *Forsythiae fructus*, together with *Sophorae tonkinesis radix, Curcumae longae rhizoma*, etc., supplements trace elements in human body and has an ability to regenerate hepatic cells.

*Paeoniae radix rubra* acts mainly on liver, spleen, etc. and exhibits anti-inflammatory and anti-ulcerative activities. It also has anti-bacterial, antipyretic, analgesic, sedative and anti-spasmodic activities. As the result obtained from in vitro test utilizing extracted hearts of tissue from a rat, it has been reported that *Paeoniae radix* rubra acts on the circulatory system to increase the blood volume in coronary arteries.

*Gentianae scabrae radix* has a liver protective and cholagogue activity to treat acute hepatic disorder caused by carbon tetrachloride in mouse and reduce the lesion of liver tissues. In addition, *Gentianae scabrae radix* also has stomachic, anti-bacterial and anti-inflammatory activities, effect on nervous system, hypotensive activity, etc. According to the result of toxicity test in mouse, it has been disclosed that since the $LD_{50}$ value of *Gentianae scabrae radix* is 460–1250 mg/kg, in case of oral administration and 163.4 g/kg in case of intravenous injection, it is substantially non-toxic.

*Acori graminei rhizoma* acts on liver, spleen and heait and has a potent anti-bacterial activity. It also has a spasmolytic activity on smooth muscle to stimulate the secretion of digestive juice, inhibit the abnormal fermentation in gastrointestinal tract and dilate the smooth muscle of intestinal tract.

In the injectable composition (A) of the galenic preparation according to the present invention, *Hedyotidis herba, Polygoni cuspidati radix, Sophorae tonkinesis radix* and *Curcumae longae rhizoma* are combined in the ratio of 2–10:2–10:2–10:0.1–5, preferably in the ratio of 4–6:4–6:4–6:1–3, on the basis of dry weight of respective natural drug.

In particularly preferred injectable composition (A), *Hedyotidis herba, Polygoni cuspidati radix, Sophorae tonkinesis radix* and *Curcumae longae rhizoma* are combined in the ratio of 5:5:5:2 on the basis of weight.

The above constitutional ratio is established in consideration of effective amounts and side effects of each main natural drug. If the constitutional ratio is beyond the above range, the pharmacological effect may be rapidly reduced or any side effect may occur.

In order to obtain a more potent activity for treating viral hepatitis B, if desired, the injectable composition (A) of the present invention can additionally contain one or more supplementary natural drugs selected from the group consisting of *Isatidis Folium, Sophorae radix, Artemisiae capillaris herba, Bupleuri radix, Atiactylodis rhizoma alba, Alisma rhizoma,* Cordyceps, *Rhei rhizoma, Isatidis Radix, Gentianae scabrae radix, Scutellariae radix* and *Paridis rhizoma*.

When the supplementary natural drugs are added to the injectable composition of the present invention, on the basis of diy weight, each of *Isatidis Folium, Sophorae radix, Aitemisiae capillaris herba, Bupleuri radix, Atractylodis rhizoma alba, Alisma rhizoma, Isatidis Radix, Gentianae scabrae radix, Scutellaniae radix* and *Paridis rhizoma* is added in the ratio of 2–10 parts by weight, preferably of 4–6 palts by weight; and each of Cordyceps and *Rhei rhizoma* is added in the ratio of 0.5–6 parts by weight, preferably of 2–4 parts by weight.

The injectable composition (A) of the present invention can be prepared according to the method conventionally used in the pharmaceutical field utilizing a pharmaceutically acceptable excipient. For example, the injectable composition (A) can be prepared according to the method for preparing injections described in the general rules of Korea Pharmacopeia, which comprises a) extracting *Curcumae longae rhizoma* with water and then distillating the water extract of *Curcumnae longae rhizoma*; b) separately extracting *Hedyotidis herba, Polygoni cuspidati radix* and *Sophorae tonkinesis radix* with water, distillating and concentrating the resulting water extract, extracting the residue thrice with ethanol and filtering the extract to obtain the filtrate; c) mixing the filtrate obtained in the step b) with the extract of *Curcumae longae rhizoma* obtained in the step a); and then d) adding thereto a pharmaceutical excipient conventionally used for preparing injections, for example, an emulsifying agent such as Tween 80.

Meanwhile, the oral composition (B) which constitutes another part of the galenic preparation according to the present invention contains 10 kinds of the main natural drugs, i.e. *Hedyotidis herba, Paridis rhizoma, Polygoni cuspidati radix, Sophorae tonkinesis radix, Gentianae scabrae radix, Rhei rhizoma, Forsythiae fructus, Paconiae radix rubra, Curcumae longae rhizoma* and *Acori graminei rhizoma*, as mentioned above.

In the oral composition (B) of the present invention, the main natural drugs are combined in the ratio of *Hedyotidis herba* 1–10, Polygoni cuspidati radix 1–10, *Sophorae tonkinesis radix* 1–10, *Paridis rhizoma* 0.5–8, *Paeoniae radix rubra* 0.5–8, *Curcumae longae rhiizoma* 0.5–8, *Acori graminel rhizoma* 0.5–8, *Gentianae scabrae radix* 0.1–5, *Rhei rhizoma* 0.1–5 and *Forsythiae fructus* 0.1–5, on the basis of their dry weights. Preferably, in the oral composition of the present invention, the main natural drugs can be combined in the ratio of *Hedyotidis herba* 3–8, *Polygoni cuspidati radix* 3–8, *Sophorae tonkinesis radix* 3–8, *Paridis rhizoma* 1–6, *Paeoniae radix rubra* 1–6, *Curcumae longae rhizoma* 1–6, *Acori graminei rhizoma* 1–6, *Gentianae scabrae radix* 0.5–4, *Rhei rhizoma* 0.5–4 and *Forsythiae fructus* 0.5–4, on the basis of dry weight.

Particularly preferred oral compositions of the present invention contain the main natural drugs in the ratio of *Hedyotidis herba: Polygoni cuspidati radix:Sophorae tonkinesis radix:Paridis rhizoma:Paeoniae radix rubra:Curcumae longae rhizoma:Acori graminei rhizoma:Gentianae scabrae radix:Rhei rhizoma:Forsythiae fructus=* 3:3:3:2:2:2:2:1:1:1 on the basis of weight.

Such constitutional ratio is established in consideration of effective amounts and side effects of each main natural drug. If the constitutional ratio is beyond the above range, the pharmacological effect may be rapidly reduced or any side effect may occur.

In order to more effectively prevent and treat fatty liver and hepatic cirrhosis, if desired, the oral composition (B) of the present invention can additionally contain one or more supplementary natural drug selected from the group consisting of Cordyceps, bear's gall-bladder, antelope's horn, *Scrophulariae radix, Salviae radix, Isatidis radix, Astiagali radix, Crataegi fructus, Imperatae rhizoma, Amydae carapax, Cumarae longae rhizoma, Angelicae gigantis radix,* Ginseng radix alba, *Lycii fructus, Schizandrae fructus, Bupleuri radix, Notoinseng radix, Artemisiae capllaris herba, Isatidis Folium* and *Scutellariae radix*.

When the supplementary natural drugs are added to the oral composition of the present invention, on the basis of dry weight, each of *Isatidis radix, Astragali radix, Crataegi fructus, Imperatae rhizoma, Cumarae longae rhizoma, Angelicae gigantis radix, Lycii fructus, Schizandrae fructus, Bupleuri radix, Notoginseng radix, Artemisiae capillaris herba, Isatidis Folium* and *Scutellariae radix* is added in the ratio of 1–10 parts by weight, preferably of 3–8 parts by weight; each of Cordyceps, antelope's horn, *Scrophulariae radix, Salviae radix, Amydae carapax* and *Ginseng radix alba* is added in the ratio of 0.5–8 parts by weight, preferably of 0.5–4 parts by weight; and bear's gall-bladder is added in the ratio of 0.01–2 parts by weight, preferably of 0.1–1 parts by weight.

The oral composition (B) of the present invention can be prepared according to the method conventionally used in the pharmaceutical field utilizing a phaimaceutically acceptable excipient. For example, the oral composition (B) can be prepared according to the process which comprises a) pulverizing *Curcumae longae rhizoma* and *Acori graminei* rhizoma; b) extracting *Hedyotidis herba, Polygoni cuspidati radix, Sophorae tonkinesis radix, Paridis rhizoma, Gentianae scabrae radix, Rhei rhizoma, Forsythiae fructus* and *Paeoniae radix rubra*; and c) combining the powder obtained in the step a) with the extract obtained in the step b).

The dosage and administration method of the galenic preparation of the present invention for the human subject can be suitably varied depending on age, sex, healthy condition of the patient, severity of the disease to be treated, the frequency of administration, etc. Generally, it is appropriate that the injectable composition (A) is intravenously injected to adult man (body weight ca, 70 kg) in a daily dosage of 1–10 ml, preferably 3–6ml, as the injection containing the extract obtained from 6–35 g of the combination of natural drugs in the above-mentioned ratio, per 1 ml. Together with this, it is also desirable that the oral composition (B) combined in the above-mentioned ratio is administered to adult man (body weight ca. 70 kg) in a daily dosage of 1–10 g. Although the injectable composition (A) and the oral composition (B) can be administered simultaneously, if required, they can also be administered at certain intervals. For this purpose, the galenic preparation of the present invention can be formulated either in the form of a kit wherein the injectable composition (A) and the oral composition (B) are contained in one package, or by separately packing two compositions in discrete packages.

The present invention is more specifically explained by the following examples and experiments. However, it should be understood that the present invention is not limited to these examples in any manner.

EXAMPLE 1

Preparation of Injectable Composition

100 G of Curcumae longae rhizoma was impregnated into water and allowed to stand for 3 hours. 1 L of distilled water was added thereto and the mixture was extracted with heating to obtain about 400–500 ml of the extract. The resulting extract was concentrated to about 250 ml to obtain the solution A.

250 G of each of *Hedyotidis herba, Sophorae tonkinesis radix* and *Polygoni cuspidati radix* were taken and mixed together, and 7 l of distilled water was then added to the mixture. This mixture was allowed to stand for 24 hours and then first extracted with heating for one hour and filtered. To the residue was added 3 l of distilled water and then extracted with heating for 40 minutes. The extracts were combined and concentrated to about 600 ml to obtain the solution B. This solution B was purified by extracting thrice with ethanol to remove impurities according to the following manner.

1400 ml of ethanol was added to the solution B to prepare the 70% ethanol solution which was allowed to stand for 24 hours and then filtered. Ethanol was removed by evaporation from 2000 ml of the resulting filtrate to obtain 600 ml of the solution B1.

To the solution B1 was added 2400 ml of 100% ethanol to obtain approximately 80% ethanol solution, which was allowed to stand for 24 hours and then filtered to obtain 3000 ml of the filtrate. The filtrate was adjusted to pH 8–9 with 20% sodium hydroxide, allowed to stand for 24–48 hours under cooling (0–4° C.) and then filtered to obtain 3000 ml of the filtrate. Ethanol was evaporated from the filtrate to obtain 600 ml of the solution B2.

To the solution B2 was added 3400 ml of ethanol to obtain 85% ethanol solution, which was allowed to stand for 24 hours under cooling (0–4° C.) and then filtered. 4000 ml of the resulting filtrate was evaporated and concentrated to 600 ml to obtain the solution B3.

The resulting solution B3 was mixed with 250 ml of the solution A as obtained above and 3 g of Tween 80 and then the mixture was adjusted by adding distilled water to about 1 l of the total volume. The resulting solution was adjusted to pH 7.5–8.0 with 2N NaOH and then prepared in the form of an injectable preparation according to the method for preparing injections described in the general rules of Korea Pharmacopeia.

EXAMPLE 2

Preparation of Oral Composition (tablets)

30 g of *Curcumae longae rhizoma* and 30 g of *Acori graminei rhizoma* were finely ground to obtain the powder A. Separately, 45 g of each of *Hedyotidis herba, Polygoni cuspidati radix* and *Sophorae tonkinesis radix*, 30 g of each of *Paridis rhizoma* and *Paeoniae radix rubra* and 15 g of each of *Gentianae scabrae radix, Rhei rhizoma* and *Forsythiae fructus* were taken and mixed together. 2.4 L of water was added to this mixture and allowed to stand for 24 hours. The mixture was extracted with heating for 1.5 hours, cooled and then filtered to obtain the filtrate B and the residue. The residue was extracted with about 1.6 l of water for one hour under heating, cooled and then filtered to obtain the filtrate. This filtrate was combined with the filtrate B as obtained above. The combined filtrate was concentrated with heating and then cooled to obtain the solution C. The powder A as obtained above was added to the solution C and thoroughly mixed together. The resulting mixture was dried at the temperature below 60° C., cooled and then pulverized to obtain 74.4 g of the powder of the mixture of natural drugs (wherein the yield of the solution C as the extract is 14.4 g (about 6%) and the total yield of natural drugs is about 24.8%). The obtained powder was formulated into a tablet according to the method for preparing tablets described in the general rules of Korea Phairacopeia to produce the tablets containing 800 mg of the powder of mixed natural drugs per one tablet.

EXAMPLE 3

Preparation of Oral Composition (capsules)

30 g of each of *Curcumae longae rhizoma, Ginseng radix alba, Lycii fructus, Schizandrae fructus, Acori graminei rhizoma, Bupleuri radix, Artemisiae capillaris herba, Isatidis Folium* and *Scutellariae radix* and 15 g of each of *Amydae carapax, Cumarae longae rhizoma* and *Angelicae gigantis radix* were finely ground to obtain the powder A. Separately, 45 g of each of *Hedyotidis herba, Polygoni cuspidati radix* and *Sophorae tonkinesis radix*, 30 g of each of *Paridis rhizoma, Astragali radix, Crataegi fructus, Paeoniae radix rubra* and *Imperatae rhizoma*, and 15 g of each of *Gentianae scabrae radix, Rhei rhizoma, Forsythiae fructus* and *Notoginseng radix* were taken and mixed together. About 3.5 l of water was added to this mixture and allowed to stand for 24 hours. The mixture was extracted with heating for 1.5 hours, cooled and then filtered to obtain the filtrate B and the residue. The residue was extracted with 2.5 l of water for one hour under heating, cooled and then filtered to obtain the filtrate. This filtrate was combined with the filtrate B as obtained above. The combined filtrate was concentrated with heating and then cooled to obtain the solution C. The powder A as obtained above was added to the solution C and thoroughly mixed together. The resulting mixture was dried at the temperature below 60° C., cooled and then pulverized to obtain 245.7 g of the powder of the mixture of natural drugs (wherein the yield of the solution C as the extract is 20.7 g (about 6%) and the total yield of natural drugs is about 70%). The obtained powder was formulated into a hard gelatine capsule according to the method for preparing capsules described in the general rules of Korea Pharmacopeia to produce the hard gelatine capsules containing 500 mg of the powder of mixed natural drugs per one capsule.

The injection as prepared in Example 1 above and the oral formulation as prepared in Example 2 or 3 were finally either produced in the form of a kit in which two foimulations are included in one package or packed in discrete packages, respectively, so as to be used concurrently when they are used for the clinical purpose.

In order to conform the preventive and therapeutic effect on hepatocarcinoma of the galenic preparation according to the present invention in which the injectable composition (A) and the oral composition (B) are combined, the following experiments were conducted. In the following experiments, the injectable preparation (A) represents the injection prepared in Example 1 and the oral preparation (B) represents the tablet prepared in Example 2, and the given amount of each preparation denotes the amount of the extract of natural drugs and the mixed natural drugs before they are formulated into the injection or tablet.

EXPERIMENT 1

Effect on Acute Hepatic Disease Induced by Galactosamine

As the test animal, male Sprague-Dawley rats weighing 150–200 g were arbitrary divided into the following eight (8) groups such that each group contains 10 animals:

① Normal group: Only physiological saline was administered.
② Control group: 500 mg of galactosamine was intiaperitoneally administered.
③ Test group 1: 40 mg/kg of the oral preparation (B) was administered via oral route.
④ Test group 2: 200 mg/kg of the oral preparation (B) was administered via oral route.
⑤ Test group 3: 70 μl/kg of the injectable preparation (A) was intraperitoneally administered.
⑥ Test group 4: 350 μl/kg of the injectable preparation (A) was intraperitoneally administered.
⑦ Test group 5: 40 mg/kg of the oral preparation (B) and 70 μl/kg of the injectable preparation (A) were administered via oral and intraperitoneal routes, respectively.
⑧ Test group 6: 200 mg/kg of the oral preparation (B) and 350 μl/kg of the injectable preparation (A) were administered via oral and intraperitoneal routes, respectively.

In this experiment, the oral preparation (B) was administered in the form of a suspension in physiological saline and the injectable paration (A) was administered as a dilution in 5% glucose solution. The control group and all the test groups, only except the noulial group, were intiaperitoneally given galactosamine in an amount of 500 mg/kg. Thereafter, the test groups were treated by administering the oral preparation (B) and/or the injectable preparation (A) in the afternoon every day for seven (7) consecutive days via oral and/or intrapenitoneal route. During this period, each of the normal group and the control group was given 10 ml of physiological saline via oral route. For blood analysis, blood was taken from orbital venous plexus 8 hours after the administration of the test drug and then centrifuged at 4,000 rpm for 10 minutes to obtain serum. The serum was subjected to measurement of GOT (glutamic oxaloacetic transaminase), GPT (glutamic pyruvic transaminase), ALP (alkaline phosphatase) and T-BIL (Total-bilirubin) concentrations by means of a blood analyzer. The results as obtained are described in the following Table 1.

TABLE 1

|  | GPT (IU/l) | GOT (IU/l) | ALP (IU/l) | T-BIL (mg/dl) |
|---|---|---|---|---|
| Normal group (n = 10) | 130 ± 38.2 | 152 ± 10.6 | 321 ± 34.2 | 0.34 ± 0.07 |
| Control group (n = 10) | 712 ± 68.6 | 681 ± 44.5 | 586 ± 55.1 | 1.08 ± 0.21 |
| Test group 1 (n = 10) | 382 ± 48.1* | 437 ± 31.2* | 412 ± 36.1* | 0.62 ± 0.23* |
| Test group 2 (n = 10) | 341 ± 59.2* | 391 ± 39.4* | 381 ± 27.2* | 0.79 ± 0.21* |
| Test group 3 (n = 10) | 421 ± 37.5* | 531 ± 51.2* | 498 ± 53.1* | 0.84 ± 0.11* |
| Test group 4 (n = 10) | 392 ± 48.1* | 497 ± 63.9* | 473 ± 60.7* | 0.81 ± 0.36* |
| Test group 5 (n = 10) | 213 ± 52.2* | 267 ± 32.1* | 376 ± 43.1* | 0.52 ± 0.04* |
| Test group 6 (n = 10) | 172 ± 45.1* | 207 ± 29.1* | 349 ± 57.5* | 0.41 ± 0.12* |

Note) *$p < 0.05$

As can be seen from the result described in the above Table 1, the increase in the values of GPT, GOT, ALP and T-BIL as measured in the liver damaged by galactosamine is much more weakened by the combined administration of the oral preparation (B) and the injectable preparation (A) (test groups 5 and 6) in comparison to the administration of the oral (test groups 1 and 2) or injectable preparation (test groups 3 and 4) alone. Particularly, it is also noted that the administration of a large amount (test group 6) provides the values which are more close to the values measured in the normal group, in comparison to the administration of a lower amount (test group 5). From such result, it can be identified that the galenic preparation of the present invention designed so that the injectable composition is administered in combination with the oral composition can effectively treat the hepatic disorder caused by galactosamine.

EXPERIMENT 2

Effect on Subacute Hepatic Disease Induced by Galactosamine

As the test animal, male Sprague-Dawley rats weighing 150–200 g were arbitrarily divided into the following six (6) groups such that each group contains 10 animals:

① Normal group: Only physiological saline was administered.
② Control group: 500 mg of galactosamine was intraperitoneally administered.
③ Test group 1: 40 mg/kg of the oral preparation (B) was administered via oral route.
④ Test group 2: 200 mg/kg of the oral preparation (B) was administered via oral route.
⑤ Test group 3: 40 mg/kg, of the oral preparation (B) and 70 μl/kg of the injectable preparation (A) were administered via oral and intraperitoneal routes, respectively.
⑥ Test group 4: 200 mg/kg of the oral preparation (B) and 350 μl/kg of the injectable preparation (A) were administered via oral and intraperitoneal routes, respectively.

In this experiment, the oral preparation (B) was administered in the form of a suspension in physiological saline and the injectable preparation (A) was administered as a dilution in 5% glucose solution. Each of the test groups were treated by administering per orally the oral preparation (B) alone or simultaneously with the injectable preparation (A) per intraperitoneally, in the morning every day for consecutive fourteen (14) days. During this period, each of the normal group and the control group was given 10 ml of physiological saline via oral route. Thereafter, the control group and all the test groups, only except the normal group, were intraperitoneally given galactosamine in an amount of 500 mg/kg four hours after the daily administration of the test drug during the period of 7th day from the beginning of the test drug administration to the last day. For blood analysis, blood was taken from the orbital venous plexus 24 hours after the last administration of galactosamine and then centrifuged at 4,000 rpm for 10 minutes to obtain serum. The serum was subjected to measurement of GOT, OPT, ALP and T-BIL concentrations by means of a blood analyzer. The results as obtained are described in the following Table 2.

TABLE 2

|  | GPT (IU/l) | GOT (IU/l) | ALP (IU/l) | T-BIL (mg/dl) |
|---|---|---|---|---|
| Normal group (n = 10) | 147 ± 3.9 | 124 ± 20.1 | 372 ± 6.2 | 0.37 ± 0.01 |
| Control group (n = 10) | 2305 ± 84.9 | 2415 ± 79.1 | 633 ± 29.1 | 1.42 ± 0.30 |
| Test group 1 (n = 10) | 987 ± 52.4* | 1578 ± 95.2* | 408 ± 65.2* | 0.67 ± 0.04* |
| Test group 2 (n = 10) | 753 ± 67.0* | 1251 ± 65.3* | 399 ± 44.4* | 0.45 ± 0.17* |
| Test group 3 (n = 10) | 841 ± 29.2* | 929 ± 41.2* | 273 ± 23.5* | 0.41 ± 0.04* |
| Test group 4 (n = 10) | 626 ± 81.9* | 754 ± 78.2* | 302 ± 18.9* | 0.58 ± 0.10* |

Note) $p < 0.05$

As can be seen from the result described in the above Table 2, the control group in this experiment in which the subacute liver disease is induced by administration of galactosamine for a long period shows a significant increase in all the GPT, GOT, ALP and T-BIL values in comparison to the control group in Experiment 1 in which the acute liver disease is induced and therefore, the degree of liver damage in subacute case is more serious than that in acute liver disease. In addition, as in Experiment 1, all the values of GPT, GOT, ALP and T-BIL measured in the test groups 3 and 4 to which the oral preparation (B) is administered in combination with the injectable preparation (A) are lower than those measured in the test groups 1 and 2 to which only the oral preparation (B) is administered. Particularly, it could also be noted that the administration of a large amount (test giroup 4) provides much lower values than the administration of a lower amount (test group 3).

EXPERIMENT 3

Effect on Subacute Hepatic Disease Induced by Carbon Tetrachloride (CCl$_4$)

As the test animal, male Sprague-Dawley rats weighing 150–200 g were arbitrarily divided into the following four (4) groups such that each group contains 10 animals:
① Normal group: Only physiological saline was administered.
② Control group: 25% carbon tetrachloride was administered in an amount of 3 ml/kg via oral route.
③ Test group 1: 40 mg/kg of the oral preparation (B) and 70 μl/kg of the injectable preparation (A) were administered via oral and intraperitoneal routes, respectively.
④ Test group 2: 200 mg/kg of the oral preparation (B) and 350 μl/kg of the injectable preparation (A) were administered via oral and intraperitoneal routes, respectively.

In this experiment, the oral preparation (B) was administered in the form of a suspension in physiological saline and the injectable preparation (A) was administered as a dilution in 5% glucose solution. Each of the test groups were treated by concurrently administering the oral preparation (B) and the injectable preparation (A) in the morning every day for consecutive twenty-one (21) days via oral and intraperitoneal routes, respectively. During this period, each of the normal group and the control group was given 10 ml of physiological saline via oral route. Thereafter, the control group and all the test groups, only except the normal group, were intraperitoneally given 25% galactosamine dissolved in olive oil in an amount of 3 ml/kg four hours after the daily administration of the test drug during the period of 7th day from the beginning of the test drug administration to the last day. For blood anally sis, blood was taken from the orbital venous plexus 24 hours after the last administration of carbon tetrachloede and then centrifuged at 4000 rpm for 10 minutes to obtain serum. The serum was subjected to measurement of GOT, GPT, ALP and T-BIL concentrations by means of a blood analyzer. The results as obtained agte described in the following Table 3.

TABLE 3

|  | GPT (IU/l) | GOT (IU/l) | ALP (IU/l) | T-BIL (mg/dl) |
|---|---|---|---|---|
| Normal group (n = 10) | 149 ± 3.4 | 109 ± 8.3 | 531 ± 48.1 | 0.09 ± 0.01 |
| Control group (n = 10) | 2553 ± 54.9 | 2484 ± 542.8 | 2632 ± 63.2 | 0.35 ± 0.001 |
| Test group 1 (n = 1) | 1866 ± 30.4* | 2527 ± 34.5* | 2102 ± 49.2 | 0.39 ± 0.02 |
| Test group 2 (n = 10) | 1746 ± 37.8* | 924 ± 37.9* | 1441 ± 75.7* | 0.26 ± 0.05* |

Note) $p < 0.05$

As can be seen from the result described in the above Table3, even when the liver damage is induced by carbon tetrachloride which more strongly attacks the liver than galactosamine, the galeniic preparation of the present invention designed so that the oral preparation (B) is administered in combination with the injectable preparation (A) significantly reduces all the values of GPT, GOT, ALP and T-BIL in comparison to the control group.

EXPERIMENT 4

Effect on Acute Hepatic Disease Induced by Alcohol

As the test animal, male Sprague-Dawley rats weighing 150–200 g were arbitrarily divided into the following six (6) groups such that each group contains 10 animals:
① Normal group: Only physiological saline was administered.
② Control group: Alcohol was orally administered in an amount of 6 g/kg.
③ Test group 1: 40mg/kg of the oral preparation (B) was administered via oral route.
④ Test group 2: 200 mg/kg of the oral preparation (B) was administered via oral route.

⑤ Test group 3: 40 mg/kg of the oral preparation (B) and 70 μl/kg of the injectable preparation (A) were administered via oral and intraperitoneal routes, respectively.

⑥ Test group 4: 200 mg/kg of the oral preparation (B) and 350 μl/kg of the injectable preparation (A) were administered via oral and intraperitoneal routes, respectively.

In this experiment, the oral preparation (B) was administered in the form of a suspension in physiological saline and the injectable preparation (A) was administered as a dilution in 5% glucose solution. Each of the test groups were treated by administering per orally the oral preparation (B) alone or simultaneously with the injectable preparation (A) per intraperitoneally, in the morning every day for consecutive fourteen (14) days. During this period, each of the normal group and the control group was given 10 ml of physiological saline via oral route. Thereafter, the control group and all the test groups, only except the normal group, were given alcohol orally in an amount of 6 g/kg in the afternoon of the last day of the test drug administration. For blood analysis, blood was taken from orbital venous plexus 24 hours after the last administration of alcohol, allowed to stand for about 30 minutes and then centrifuged to obtain serum. The triglyceride (TG) activity in the serum was determined by measuring the optical density at 450 nm on the basis of free glycerol specific-extinction method. The results as obtained are described in the following Table 4.

TABLE 4

| Groups | Normal group (n = 10) | Control group (n = 10) | Test group 1 (n = 10) | Test group 2 (n = 10) | Test group 3 (n = 10) | Test group 4 (n = 10) |
|---|---|---|---|---|---|---|
| TG(mg/dl) | 20.7 ± 10.6 | 45.4 ± 17.7 | 26.2 ± 9.1* | 30.7 ± 7.0* | 39.5 ± 9.9 | 31.6 ± 6.7* |

Note) *p < 0.05

As can be seen from the result described in the above Table 4, in the case of acute liver disease induced by alcohol the galenic preparation of the present invention designed so that the oral preparation (B) is administered in combination with the injectable preparation (A) significantly reduces the activity of tiglyceride in comparison to the control group. Therefore, it could be noted that the galenic preparation of the present invention is effective for the prevention of liver from acute liver damage caused by alcohol.

EXPERIMENT 5

Effect on Subacute Hepatic Disease Induced by Alcohol

As the test animal, male Sprague-Dawley rats weighing 150–200 g were arbitrarily divided into the following six (6) groups such that each group contains 10 animals:

① Normal group: Only physiological saline was administered.

② Control group: Alcohol was orally administered in an amount of 6 g/kg.

③ Test group 1: 40 mg/kg of the oral preparation (B) was administered via oral route.

④ Test group 2: 200 mg/kg of the oral preparation (B) was administered via oral route.

⑤ Test group 3: 40 mg/kg of the oral preparation (B) and 70 μl/kg of the injectable preparation (A) were administered via oral and intraperitoneal routes, respectively.

⑥ Test group 4: 200 mg/kg of the oral preparation (B) and 350 μl/kg of the injectable preparation (A) were administered via oral and intraperitoneal routes, respectively.

In this experiment, the oral preparation (B) was administered in the form of a suspension in physiological saline and the injectable preparation (A) was administered as a dilution in 5% glucose solution. Each of the test groups were treated by administering orally the oral preparation (B) alone or simultaneously with the injectable preparation (A) intraperitoneally, in the morning every day for consecutive twenty-one (21) days. During this period, each of the normal group and the control group was given 10 ml of physiological saline via oral route. Thereafter, the control group and all the test groups, only except the normal group, were given alcohol orally in an amount of 6 g/kg during the period of 7th day from the beginning of the test drug administration to the last day. For blood analysis, blood was taken from orbital venous plexus 24 hours after the last administration of alcohol, allowed to stand for about 30 minutes and then centrifuged to obtain serum. The triglyceride (TG) activity in the serum was determined by measuring the optical density at 450 nm on the basis of free glycerol specific-extinction method. The results as obtained are described in the following Table 5.

TABLE 5

| Groups | Normal group (n = 10) | Control group (n = 10) | Test group 1 (n = 10) | Test group 2 (n = 10) | Test group 3 (n = 10) | Test group 4 (n = 10) |
|---|---|---|---|---|---|---|
| TG(mg/dl) | 23.62 ± 17.36 | 56.28 ± 20.24 | 26.0 ± 7.7* | 27.9 ± 8.5* | 25.8 ± 9.5* | 20.7 ± 3.8* |

Note) *p < 0.05

As can be seen from the result described in the above Table 5, in the case of liver disease induced by long-term administration of alcohol the galenic preparation of the present invention designed so that the oral preparation (B) is administered in combination with the injectable preparation (A) significantly reduces the activity of triglyceride in comparison to the control group. Therefore, it could be noted that the galenic preparation of the present invention is effective for the prevention of liver from liver damage caused by continuous drinking of alcohol.

EXPERIMENT 6

Effect on Chronic Hepatocarcinoma

As the test animal, male Fisher 344 rats weighing 150–200 g were arbitrarily divided into the following four (4) groups such that each group contains 10 animals:

① Normal group: Only physiological saline was administered.

② Control group: DEN (diethylnitrosoamine) and 0.03% AAF (acetaminofluorene) were orally administered.

③ Test group 1: 40 mg/kg of the oral preparation (B) and 70 μl/kg of the injectable preparation (A) were administered via oral and intraperitoneal routes, respectively.

④ Test group 2: 200 mg/kg of the oral preparation (B) and 350 μl/kg of the injectable preparation (A) were administered via oral and intraperitoneal routes, respectively.

In the test animals, hepatocarcinoma was induced according to Solt-Farber standard method [see, Solt D. and Farber E. (1976), New principle for analysis of chemical carcinogenesis, Nature 263: 706–708] as described below. DEN (diethylnitrosoamine) was intraperitoneally administered in an amount of 200 mg/kg, and after 2 weeks, 0.03% AAF (acetaminofluorene) was administered for 10 weeks via oral route. After three (3) weeks from the 10 weeks administration of AAF, 50% hemihepatectomy was conducted to induce hepatocarcinoma. During the overall period (i.e. 12 weeks) for administration of oncogenic materials (DEN and AAF), each of the normal group and the control group was given 10 ml of physiological saline via oral route, and the test groups 1 and 2 were given the galenic preparation according to the present invention in an amount stated above.

For serological analysis, blood was taken from venae cava abdominalis of test animals which survive to the end of the experiment and then centrifuged in a microcentrifuge tube at 4,000 rpm for 10 minutes to separate the serum. The separated serum was subjected to measurement of the enzymatic activity of GOT and GPT, the activity of ALP, and T-BIL by means of a blood analyzer. In addition, the triglyceride (TG) activity in the serum was determined by measuring the optical density at 540 nm on the basis of fiee glycerol specific-extinction method. The results as obtained are described in the following Table 6.

TABLE 6

|  | GPT (IU/l) | GOT (IU/l) | ALP (IU/l) | T-BIL (mg/$\mu$l) | TG (mg/dl) |
| --- | --- | --- | --- | --- | --- |
| Normal group (n = 10) | 15 ± 2.8 | 71 ± 6.5 | 479 ± 42.8 | 0.2 ± 0.02 | 32 ± 7.1 |
| Control group (n = 10) | 106 ± 17.2 | 182 ± 35.3 | 229 ± 36.1 | 0.64 ± 0.12 | 199 ± 18.3 |
| Test group 1 (n = 10) | 83 ± 9.4 | 139 ± 21.2 | 207 ± 15.5 | 0.45 ± 0.11 | 94 ± 10.7 |
| Test group 2 (n = 10) | 73 ± 4.6 | 110 ± 10.1 | 171 ± 19.8* | 0.33 ± 0.02* | 78 ± 16.1* |

Note) *<0.05

As can be seen firom the result described in the above Table 6, in hepatocarcinoma-induced rats the galenic preparation of the present invention designed so that the oral preparation (B) is administered in combination with the injectable preparation (A) significantly reduces all the values of GPT, GOT, ALP, T-BIL and TG in comparison to the control group. Therefore, it could be noted that the galenic preparation of the present invention can effectively inhibit the development of hepatocarcinoma.

Figure 2:
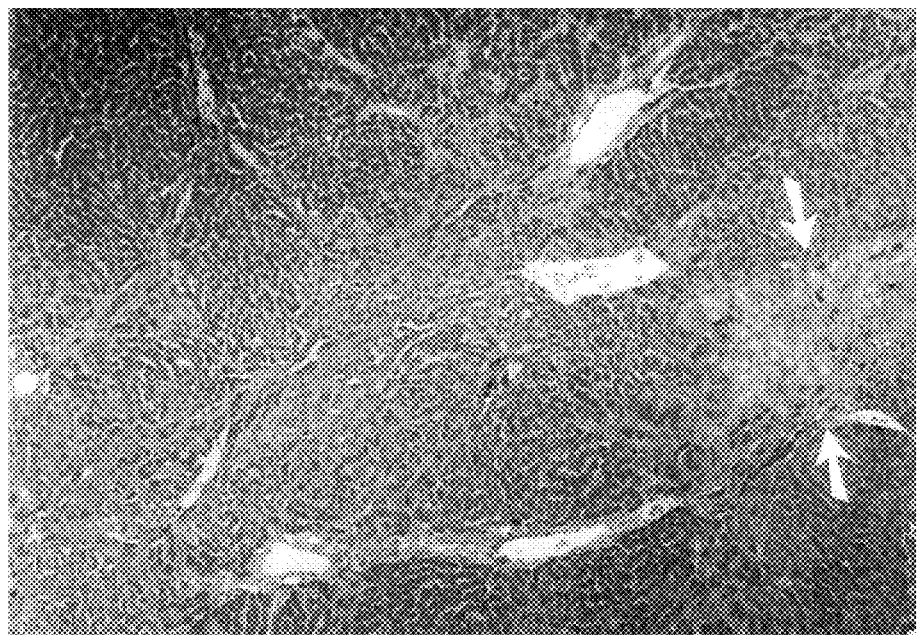
FIG. 2 is a photograph of rat liver of the control group in which chronic hepatocarcinoma is induced by DEN and AAF according to Experiment 6 (Masson-Trichrome staining; Arrow denotes fibrosis)
Figure 3:
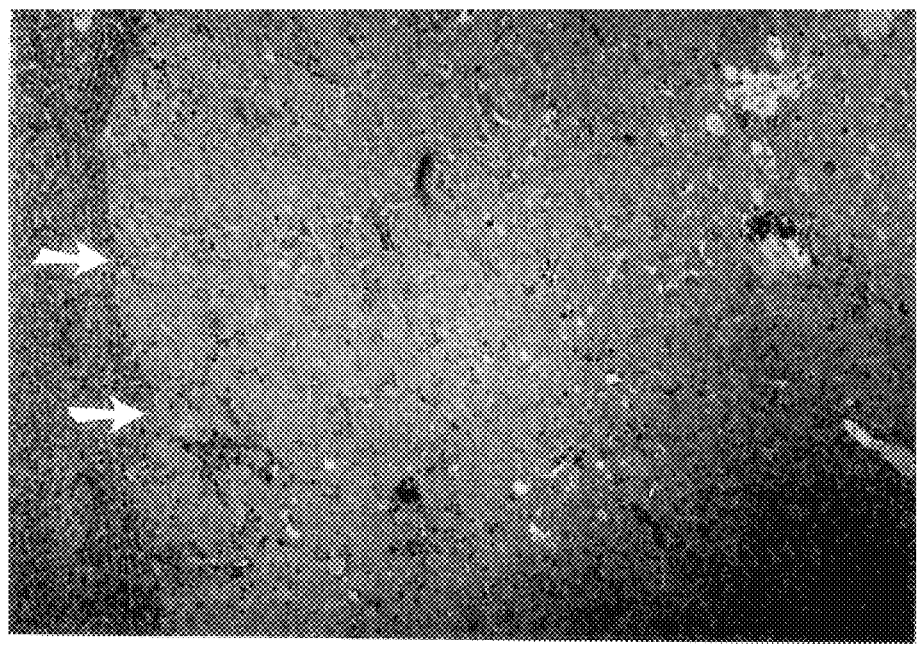
FIG. 3 is a photograph of rat liver of the control group in which chronic hepatocarcinoma is induced by DEN and AAF according to Experiment 6 (H&E (Hematoxylin and Eosin) staining; Arrow denotes large nodulus)
Figure 4:
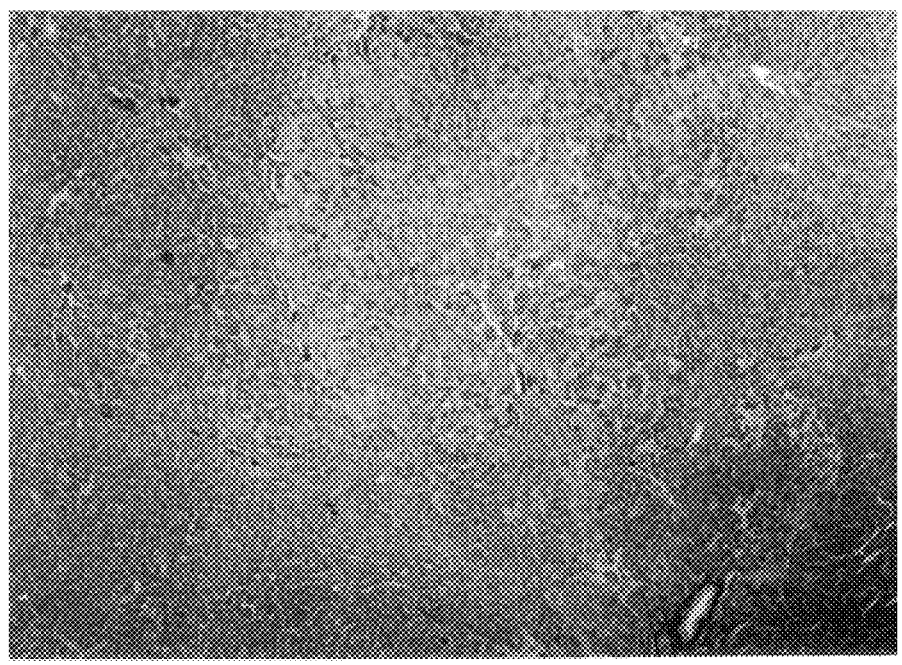
FIG. 4 is a photograph of rat liver of the test group 2 in which chronic hepatocarcinoma is induced by DEN and AAF and then the combination of 200 mg/kg of the oral composition and 350 μl/kg of the injectable composition is administered according to Experiment 6 (Masson-Trichrome staining)
Figure 5:
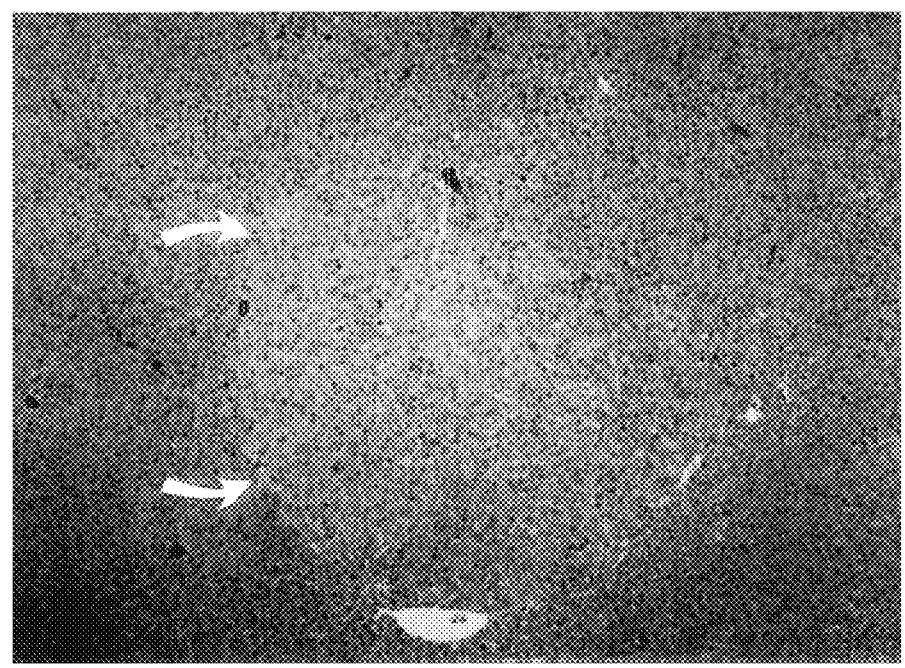
FIG. 5 is a photograph of rat liver of the test group 2 in which chronic hepatocarcinoma is induced by DEN and AAF and then the combination of 200 mg/kg of the oral composition and 350 μl/kg of the injectable composition is administered according to Experiment 6 (H&E staining; Arrow denotes small nodules).

In addition, after completion of the experiment, liver was extracted from respective test animal and then macroscopically observed. The results are shown in FIG. 1. As can be seen firom FIG. 1, in comparison to the normal group, nodes could be clearly observed in the control group but were small and unclear in the test groups 1 and 2 to which the galenic preparation of the present invention is administered, according to the macroscopic view. Therefore, it was observed that by administration of the galenic preparation of the present invention the degree of development of hepatocarcinoma significantly differs from that in the control group. Further, the liver tissues of rats in the control group and the test group 2 were stained with Masson-Trichrome (FIGS. 2 and 4) or H&E (hematoxylin and cosin) (FIGS. 3 and 5), respectively. As a result, it could be observed the liver of the control group (FIGS. 2 and 3) shows fibrosis and clear nodules and most cells have scarlet cytoplasm and clear nuclear. Contrary to this, in liver of the test group 2 fibrosis and clear nodules, as in the control group were not observed but the change of many cells into eosinophilic cells, transparent cells or vaculous cells were observed and the sizes of nucleus and nucleolus were smaller than those in the control group. From such result, it could be considered that the galenic preparation of the present invention can inhibit the fibrosis of liver and the excessive proliferation of hepatocytes.

EXPERIMENT 7

Effect on Chronic Hepatocarcinoma of the Galenic Preparation of the Present Invention in Comparison to the Combination of Yongdamsakantang and *Polygoni cuspidati* Radix The following test was conducted in order to compare the effect of the galenic preparation according to the present invention on hepatocarcinoma with that of the combination of Yongdamsakantang (*Gentianae scabrae radix, Rehmaniae radix crudae, Bupleuri radix, Crataegi fructus, Scutellariae radix, Akebiae lignum, Plantaginis semen, Alisma rhizoma, Angelicae gigantis radix, Glycyrrhizae radix*), which has been known as being relatively effective for hepatocarcinoma, and the extract of *Polygoni cuspidati radix*.

As the test animal, male SD rats weighing 150–200 g were arbitrarily divided into the following four (4) groups such that each group contains 10 animals:

① Normal group: Only physiological saline was administered.

② Control group: DEN and 0.03% AAF were orally administered.

③ Test group 1: 200 mg/kg of the oral preparation (B) and 350 $\mu$l/kg of the injectable preparation (A) were administered via oral and intraperitoneal routes, respectively.

④ Test group 2: 200 mg/kg of Yongdamsakantang and 200 mg/kg of the extract of *Polygoni cuspidati radix* were orally administered together.

In the test animals, hepatocarcinoma was induced according to Solt-Farber standard method in the following manner. DEN was intraperitoneally administered in an amount of 200 mg/kg, and after 2 weeks, 0.03% AAF was administered for 10 weeks via oral route. After three (3) weeks from the 10 weeks administration of AAF, 50% hemihepatectomy was conducted to induce hepatocarcinoma. During the overall period (i.e. 12 weeks) for administration of oncogenic materials (DEN and AAF), each of the normal group and the control group was given 10 ml of physiological saline via oral route, and the test groups 1 and 2 were given the test preparations in an amount stated above.

For serological analysis, blood was taken fiom venae cava abdominalis of test animals which suirvive to the end of the experiment and then centrifuged in a microcentrifuge tube at 4,000 rpm for 10 minutes to separate the serum. The separated serum was subjected to measurement of the enzymatic activity of GOT and GPT, the activity of ALP, and T-BIL by means of a blood analyzer. The results as obtained are described in the following, Table 7.

TABLE 7

|  | GPT (IU/l) | GOT (IU/l) | ALP (IU/l) | T-BIL (mg/dl) |
|---|---|---|---|---|
| Normal group (n = 10) | 121 ± 18.2 | 139 ± 3.8 | 278 ± 5.2 | 0.27 ± 0.1 |
| Control group (n = 10) | 2455 ± 9.8 | 1891 ± 4.2 | 658 ± 11.2 | 1.52 ± 0.3 |
| Test group 1 (n = 10) | 259 ± 5.3 | 542 ± 7.0 | 399 ± 4.9 | 0.58 ± 0.04 |
| Test group 2 (n = 10) | 928 ± 4.9 | 965 ± 12.1 | 428 ± 3.3 | 0.67 ± 0.3 |

Note) $p < 0.05$

As can be seen from the result described in the above Table 7, in hepatocarcinoma-induced rats the test group 1 treated with the g(alenic preparation of the present invention designed so that the oral preparation (B) is administered in combination with the injectable preparation (A) significantly reduces all the values of GPT, GOT, ALP and T-BIL in comparison to the test group 2 to which the combination of Yongdamsakantang and the extract of *Polygoni cuspidati radix* is administered. Therefore, it can be seen that the galenic preparation of the present invention can more effectively inhibit the development of hepatocarcinoma in comparison to the known galenic preparation.

What is claimed is:

1. A galenic preparation for treatment of hepatocarcinoma which comprises, an injectable composition (A) comprising *Hedyotidis herba, Curcumae longae rhizoma, Polygoni cuspidati radix* and *Sophorae tonkinesis radix* contained in the ratio of 2–10:2–10:2–10:0.1–5 on the basis of the total dry weight of *Hedyotidis herba, Curcumae longae rhizoma, Polygoni cuspidati radix* and *Sophorae tonkinesis radix*; and an oral composition (B) comprising *Hedyotidis herba, Paridis rhizoma, Polygoni cuspidati radix, Sophorae tonkinesis radix, Gentianae scabrae radix, Rhei rhizoma, Forsythiae fructus, Paeoniae radix rubra, Curcumae longae rhizoma* and *Acori graminei rhizoma* contained in the ratio of 1–10:1–10:1–10:0.5–8:0.5–8:0.5–8:0.5–8:0.1–5:0.1–5:0.1–5 on the basis of the total dry weight of *Hedyotidis herba, Paridis rhizoma, Polygoni cuspidati radix, Sophorae tonkinesis radix, Gentianae scabrae radix, Rhei rhizoma, Forsythiae fructus, Paeoniae radix rubra, Curcumae longae rhizoma* and *Acori graminei rhizoma*.

2. The galenic preparation for treatment of hepatocarcinoma according to claim 1, wherein in the injectable composition (A) *Hedyotidis herba, Curcumae longae rhizoma, Polygoni cuspidati radix* and *Sophorae tonkinesis radix* are contained in the ratio of 5:5:5:2 on the basis of the total dry weight of *Hedyotidis herba, Curcumae longae rhizoma, Polygoni cuspidati radix* and *Sophorae tonkinesis radix*.

3. The galenic preparation for treatment of hepatocarcinoma according to claim 1, wherein the injectable composition (A) further comprises at least one of *Isatidis Folium, Sophorae radix, Artemisiae capillaris herba, Bupleuri radix, Atractylodis rhizoma alba, Alisma rhizoma*, Cordyceps, *Rhei rhizoma, Isatidis Radix, Gentianae scabrae radix, Scutellariae radix* and *Paridis rhizoma*.

4. The galenic preparation for treatment of hepatocarcinoma according to claim 1, wherein in the oral composition (B) *Hedyotidis herba, Paridis rhizoma, Polygoni cuspidati radix, Sophorae tonkinesis radix, Gentianae scabrae radix, Rhei rhizoma, Forsythiae fructus, Paeoniae radix rubra, Curcumae longae rhizoma* and *Acori graminei rhizoma* are contained in the ratio of 3:3:3:2:2:2:2:1:1:1 on the basis of the total dry weight of *Hedyotidis herba, Paridis rhizoma, Polygoni cuspidati radix, Sophorae tonkinesis radix, Gentianae scabrae radix, Rhei rhizoma, Forsythiae fructus, Paeoniae radix rubra, Curcumae longae rhizoma* and *Acori graminei rhizoma*.

5. The galenic preparation for treatment of hepatocarcinoma according to claim 1, wherein the oral composition (B) further comprises at least one of Cordyceps, bear's gallbladder, antelope's horn, *Scrophulariae radix, Salviae radix, Isatidis Radix, Astragali radix, Crataegi fructus, Imperatae rhizoma, Amydae carapax, Cumarae longae rhizoma, Angelicae gigantis radix, Ginseng radix alba, Lycii fructus, Schizandrae fructus, Bupleuri radix, Notoginseng radix, Artemisiae capillaris herba, Isatidis Folium* and *Scutellariae radix*.

* * * * *